United States Patent [19]

Freeman et al.

[11] 3,965,489

[45] June 29, 1976

[54] ENDOPROSTHETIC BONE JOINT DEVICE FOR THE TALO-NAVICULAR JOINT

[75] Inventors: Michael Alexander Reykers Freeman, London; Geoffrey Edward Kempson, Flackwell Heath; Michael Anthony Tuke, Sutton, all of England

[73] Assignee: National Research Development Corporation, London, England

[22] Filed: Apr. 9, 1975

[21] Appl. No.: 566,431

[30] Foreign Application Priority Data
Apr. 11, 1974 United Kingdom............... 16182/74

[52] U.S. Cl.................................. 3/1.91; 128/92 C
[51] Int. Cl.² ........................................... A61F 1/24
[58] Field of Search.......................... 3/1, 1.9–1.913; 128/92 C, 92 CA

[56] References Cited
UNITED STATES PATENTS 3,521,302   7/1970   Muller............................... 3/1.91
3,896,502   7/1975   Lennox................................ 3/1.91

*Primary Examiner*—Ronald L. Frinks
*Attorney, Agent, or Firm*—Cushman, Darby & Cushman

[57] ABSTRACT

An endoprosthetic bone joint device for the talo-navicular joint comprises two generally similar components each of disc form with one face curved to define a bearing surface and the other face provided with an elongated, relatively shallow, relieved configuration extending across the latter face, the components differing by having complementary bearing surfaces of respectively convex and concave shape. The bearing surface shapes are suitably spherical and the relieved configurations provided by a longitudinally tapered rib with undercut side faces. In use, the joint is approached from above, the bones formed with downward slots to receive the component ribs by translation, and the components with convex and concave bearing surfaces respectively cemented to the talus and navicular.

6 Claims, 6 Drawing Figures

ENDOPROSTHETIC BONE JOINT DEVICE FOR THE TALO-NAVICULAR JOINT

This invention concerns articulatory endoprosthetic bone joint devices and more particularly such devices for the talo-navicular joint.

An object of the present invention is to provide a device for this last joint, which device is compatible with the relatively restricted surgical approach allowed by the joint.

Accordingly the proposed endoprosthetic talo-navicular joint device comprises: a talar component in the form of a disc having one face convexly curved to define a bearing surface, and the other face provided with a relieved configuration of elongated shape across such face but relatively shallow depth; and a navicular component of similar form to said talar component, but with the bearing surface of the former being concave and generally complementary to that of the latter for mutual articulatory bearing engagement therebetween.

Figure 1:
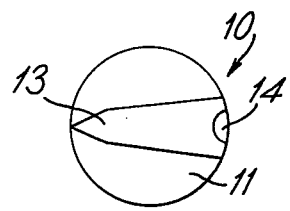
Figure 2:
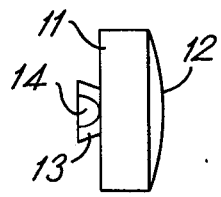
Figure 3:
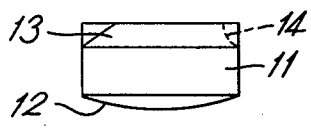
Figure 4:
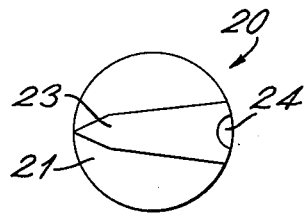
Figure 5:
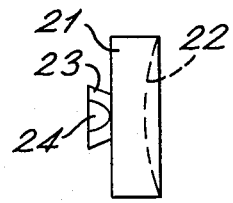
Figure 6:
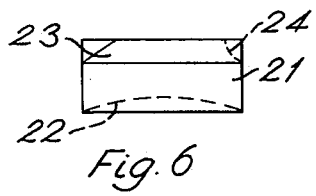

In order that the device and its intended use may be more fully understood, the same will now be described, by way of example, with reference to the accompanying drawings, in which:

FIGS. 1, 2 and 3 respectively illustrate in plane and mutually perpendicular side views the talar component of one embodiment of the invention, and FIGS. 4, 5 and 6 similarly illustrate the associated navicular component of that embodiment.

The illustrated talar component is denoted generally at 10 and comprises a main body 11 in the form of a disc which is right-circular-cylindrical. This body has one face spherically shaped to define a convex bearing surface 12, such shaping being more particularly that of a minor spherical segment coaxial with the main body 11. The other face of the body 11 is relieved to provide an upstanding part 13 of elongated form extending diametrically across the face. The part 13 extends fully across the face and is longitudinally tapered in convergent manner along the whole of its length towards one end, and this taper is further sharpened at said one end. Also, the part 13 is formed with a recess 14 at its other end portion, which recess opens into the relevant end and plan view surfaces of the part to form, together with the longitudinal convergence, arrow head or V shaping as seen in the plan view of FIG. 1. The longitudinal side faces of the part 13 are undercut to form a dovetail cross-sectional shaping as seen in the view direction of FIG. 2.

The illustrated navicular component is denoted generally at 20, and is of the same overall form and dimensions as the talar component with a body 21, bearing surface 22, upstanding part 23, and recess 24, except that the bearing surface 22 is concave and complementary to the surface 12.

A further difference between the two components in a prototype of the illustrated embodiment is that they are made from different materials, namely stainless steel and ultra high molecular weight polyethylene, respectively, to take advantage of the low friction and other desirable properties of such a metal/synthetic polymer combination. However, other choices of materials are possible.

In use of the embodiment, the talo-navicular joint is approached from the dorsal aspect of the foot to expose the talus and navicular, which bones are retracted to the extent that the remaining intact capsule allows and prepared by slotting the same, from above, downwardly across their mutually facing surfaces to receive the upstanding parts 13 and 23 and the adjacent portions of the bodies 11 and 21. The components are located this way by translation in the longitudinal directions of their parts 13 and 23. Securement of each component involves the use of a suitable acrylic cement or other gap-filling medium between the relevant bone and component, such medium being applied to the bone first, and the component being applied thereafter with the part 13 or 23 convergent end foremost to urge the medium firmly between the component and bone. As a final step in securement, cement is applied between the component and a small hole in the adjacent bone to fill the recess 14 or 24.

Upon surgical closure the two components are held with their surfaces 12 and 22 in bearing engagement to afford articulatory capability similar to that of the natural joint.

While the invention has been described with more particular reference to the illustrated embodiment, the latter represents a presently preferred form of the invention rather than a limitation thereon and variations of this form are possible with the broader scope of the invention. For example, the more particular features of design of the parts 13 and 23 serve a variety of roles in securement of the components with cement in that the elongate form acts against rotation of the component about its axis, the undercut sides of these parts act against separation from the bone along the component axis, the recesses in these parts serve against separation from the bone by translation in the longitudinal direction of the parts 13 and 23, and the tapered form of these parts assist in urging the cement to fill the component/bone spaces. However, the elongate form of these fixation parts is their primary feature in facilitating component location and securement within the limits of the available surgical approach and exposure, and other features and also the numbers, of such parts clearly can be varied.

Also while the use of sperically shaped bearing surfaces is considered particularly advantageous, it is possible that these also can be varied.

We claim:

1. An endoprosthetic talo-navicular joint device comprising: a talar component in the form of a disc having one face convexly curved to define a bearing surface, and the other face provided with a relieved configuration of elongated shape across such face but relatively shallow depth, said configuration including a rib which is longitudinally convergently tapered towards one end thereof and extends across said other face; and a navicular component of similar form to said talar component, but with the bearing surface of the former being concave and generally complementary to that of the latter for mutual articulatory bearing engagement therebetween.

2. A device according to claim 1 wherein the rate of said convergence is increased towards said rib one end.

3. A device according to claim 1 wherein the other end of said rib is notched to define a generally bifurcated shape.

4. A device according to claim 1 wherein said rib has undercut longitudinal side faces.

5. A device according to claim 1 wherein said convex and concave bearing surfaces are substantially spherically shaped, and said rib has undercut longitudinal side faces.

6. The use of an endoprosthetic bone joint device:

which device comprises a first component and a second component each of generally similar disc form with one disc face curved to define a bearing surface, and the other disc face provided with a relieved configuration of elongated shape across such other face, but with said first and second components differing by said bearing surfaces being of complementary respectively convex and concave shape;

and which use comprises applying said device to the talo-navicular joint by approaching said joint in the dorsal aspect to expose the talus and navicular bones, retracting said bones, forming the mutually facing surfaces of said bones from above to provide downwardly directed slots generally complementary to said relieved configuration, applying gap-filling cement to said slots, respectively locating said relieved configuration of said first and second components in said slots of the talus and navicular, and closing said joint to bring said bearing surfaces into mutual articulatory engagement.

\* \* \* \* \*